United States Patent [19]

Saito et al.

[11] Patent Number: 5,429,590
[45] Date of Patent: Jul. 4, 1995

[54] MEDICAL WATER-ABSORPTIVE POLYMER AND DRESSING FOR WOUND AND MEDICAL BANDAGE USING THE SAME

[75] Inventors: Junichi Saito; Tetsuji Sugii; Toshiyuki Yamamoto, all of Osaka, Japan

[73] Assignee: Nitto Denko Corporation, Osaka, Japan

[21] Appl. No.: 159,241

[22] Filed: Nov. 30, 1993

[30] Foreign Application Priority Data

Dec. 1, 1992 [JP] Japan .................................. 4-349734
Jan. 14, 1993 [JP] Japan .................................. 5-021845

[51] Int. Cl.⁶ ............................................. A61F 13/00
[52] U.S. Cl. ................................ 602/48; 602/54; 602/42; 604/368
[58] Field of Search ................... 602/42, 48, 54, 55, 602/903; 604/364, 368, 372

[56] References Cited

U.S. PATENT DOCUMENTS

| | | | |
|---|---|---|---|
| 2,940,868 | 6/1960 | Patchell | 602/55 |
| 3,577,516 | 5/1971 | Gould et al. | 424/46 |
| 4,074,039 | 2/1978 | Lim et al. | 602/48 |
| 4,442,258 | 4/1984 | Sunakawa et al. | 524/767 |
| 4,880,416 | 11/1989 | Horiuchi et al. | 604/307 |
| 5,298,258 | 3/1994 | Akemi et al. | 424/484 |

FOREIGN PATENT DOCUMENTS

| | | |
|---|---|---|
| 0023395 | 2/1981 | European Pat. Off. . |
| 0201828 | 11/1986 | European Pat. Off. . |
| 0268680 | 6/1988 | European Pat. Off. . |
| 0296787 | 12/1988 | European Pat. Off. . |
| 2190387 | 11/1987 | United Kingdom . |

*Primary Examiner*—Paul Prebilic
*Attorney, Agent, or Firm*—Sughrue, Mion, Zinn, Macpeak & Seas

[57] ABSTRACT

A medical water-absorptive polymer, a dressing for wound using the polymer and a medical bandage using the polymer are disclosed. The medical water-absorptive polymer comprising a medical water-absorptive polymer comprising an acrylic copolymer obtained by copolymerizing an acrylic composition comprising from 60 to 80% by weight of an alkoxyalkyl acrylate, from 20 to 40% by weight of an N-vinyllactam, and 10% by weight or less of a vinylcarboxylic acid.

14 Claims, No Drawings

MEDICAL WATER-ABSORPTIVE POLYMER AND DRESSING FOR WOUND AND MEDICAL BANDAGE USING THE SAME

FIELD OF THE INVENTION

The present invention relates to a medical water-absorptive polymer and a dressing for a wound and a medical bandage using the polymer. More particularly, the present invention relates to a flexible, elongative, and transparent medical water-absorptive polymer expandable by absorbing water, which is used for a dressing for a wound and a medical bandage.

BACKGROUND OF THE INVENTION

About the medical treatment of a wound of the skin, such as a dermal burn, a partial thickness wound, a traumatic skin defficiency, a sore, an incised wound, etc., many research results have been reported and an expectation has been increased year by year on the utility of the so-called wet healing [reported by R. G. Geronemus, et al., J. Dermatol. Surg. Oncol., 8(10), 850(1982)] wherein the healing of a wound is accelerated without forming a crusta by keeping the wound at a wet state without dipping in water and preventing the contamination with microorganisms.

Almost all the dressings which have hitherto been applied for the wet healing cannot be said to sufficiently satisfy the preferred characteristics for the medical treatment of wounds. For example, since semi-occlusive film dressings using a polyurethane film, etc., do not have a moisture absorbing and maintaining property, when the film dressing has a high moisture permeability, the wounded portion is gradually dried to form a crusta, etc., and when the film dressing has a low moisture permeability, the wounded portion is wetted with an exudate and becomes an excessively wetted state.

Since so-called hydrocolloid dressings each comprising a rubber elastomer, etc., and a hydrocolloid component are poor in transparency, the treatment state cannot be observed from the outside and further since these hydrocolloid dressings are slightly poor in the flexibility, it is difficult to apply the dressing to a bend portion such as a joint, etc.

Furthermore, since hydrogel dressings made of a hydrophilic polymer, etc., are poor in a skin adhesive property, if the hydrogel dressing does not have a fluid absorbing and maintaining property, an exudate leaks and also it is difficult to prevent the entrance of microorganisms from the outside. In addition, a portion of the dressing, which does not take part in water absorption, is gradually dried to lose the flexibility and tends to show a physical stimulation.

Water-absorptive dry sheet-type dressings which become hydrogels by absorbing a body fluid, such as a collagen film, etc., are mostly mesh-form or nonwoven fabric dressings for imparting flexibility thereto and hence a good skin adhesive property and a microorganism intercepting property cannot be expected.

Also, conventional fixing surgical tapes, medical pressure-sensitive adhesive sheets used for a first-acid bandage, a magnetic bandage, etc., pressure-sensitive adhesive bandages having an elasticity, and pressure-sensitive adhesives used for transdermal drug delivery patch preparations, etc., are subjected to a preparation plan having sufficient air permeability and moisture permeability for preventing the occurrence of maceration but at a much sweat portion, a maceration frequently occurs to cause an inflammation.

SUMMARY OF THE INVENTION

Accordingly, one object of the present invention is to provide a medical water-absorptive polymer having excellent main characteristics, such as a water absorbing property, a skin adhesive property, a flexibility, and a transparency, for the preparation necessary for the so-called wet healing which accelerates the treatment of a wound without forming a crusta by maintaining the wound in a wet state without dipping in water and preventing the contamination with microorganisms.

Another object of the present invention is to provide a dressing for a wound and a medical bandage which do not cause maceration by sufficient water absorptive property and moisture permeability.

The medical water-absorptive polymer of the present invention is a water-absorptive polymer which is used for medical treatments to attain the above-described objects, and the water-absorptive polymer comprises an acrylic copolymer obtained by copolymerizing from 60 to 80% by weight of an alkoxyalkyl acrylate, from 20 to 40% by weight of an N-vinyllactam, and 10% by weight or less of a vinylcarboxylic acid.

Thus, the medical water-absorptive polymer of the present invention contains an alkoxyalkyl acrylate and an N-vinyllactam as the essential components.

DETAILED DESCRIPTION OF THE INVENTION

The present invention is described in detail below.

Examples of the alkoxyalkyl acrylate which is one of the essential monomers of the medial water-absorptive polymer of the present invention are 2-methoxyethyl acrylate, 2-ethoxyethyl acrylate, 2-butoxyethyl acrylate, 3-methoxypropyl acrylate, 3-methoxybutyl acrylate, 3-ethoxypropyl acrylate, and 3-ethoxybutyl acrylate. Further, alkoxyalkylene glycol acrylates such as butoxyethylene glycol acrylate, 2-(2-ethoxyethyl)ethylene glycol acrylate, methoxytriethylene glycol acrylate, methoxydipropylene glycol acrylate, etc., can be used as the monomer. In these monomers, 2-methoxyethyl acrylate, etc., having a low glass transition point and a high hydrophilic property is preferably used in the present invention.

Examples of the N-vinyllactam used in the present invention are N-vinyl-2-pyrrolidone, N-vinyl-2-piperidone, and N-vinyl-2-caprolactam. From the standpoints of a safety and a general usability, N-vinyl-2-pyrrolidone is preferred.

Examples of the vinylcarboxylic acid used in the present invention are acrylic acid, methacrylic acid, crotonic acid, itaconic acid, maleic acid, fumaric acid, a maleic acid hemiester, and a fumaric acid hemiester. From the points of the reactivity and the general usability, acrylic acid is preferred.

The medical water-absorptive polymer of the present invention comprises an acrylic copolymer obtained by copolymerizing the alkoxyalkyl acrylate and the N-vinyllactam as the essential components, if necessary, together with the vinylcarboxylic acid.

In more detail, the acrylic copolymer is the copolymer obtained by copolymerizing from 60 to 80% by weight of the alkoxyalkyl acrylate, from 20 to 40% by weight of the N-vinyllactam, and 10% by weight or less of the vinylcarboxylic acid.

The amount of the alkoxyalkyl acrylate compounded in the acrylic copolymer is from 60 to 80% by weight based on the total weight of the copolymer. If the proportion of this component is less than 60% by weight, the flexibility of the film of the copolymer is undesirably decreased and on the other hand, if the proportion of this component is over 80% by weight, the pressure-sensitive adhesion of the copolymer film obtained is undesirably increased to decrease the strength of the film.

The amount of the N-vinyllactam compounded in the acrylic copolymer is from 20 to 40% by weight based on the total weight of the copolymer. If the proportion of this component is less than 20% by weight, the strength and the water-absorbability of the copolymer film obtained are undesirably decreased and on the other hand, if the proportion of this component is over 40% by weight, the flexibility of the copolymer film obtained is undesirably decreased and the acrylic copolymer formed is dissolved in water and an exudate to form a stream, which is also undesirable.

The amount of the vinylcarboxylic acid compounded in the acrylic copolymer is 10% by weight or less. That is, the amount of the vinylcarboxylic acid is from 0 to 10% by weight based on the total weight of the copolymer and is preferably from 0 to 5% by weight. If the amount of this component is over 10% by weight, there are undesirable possibilities to accelerate the water-absorbability of the copolymer film, decrease the flexibility thereof, and decrease the wound healing ability.

The reason for compounding the vinylcarboxylic acid in the present invention is to further improve the water absorbability but if the amount thereof is over 10% by weight, a stanching property is decreased to cause a possibility to delay the treatment of a wound. For this reason, it is particularly preferred that the amount of the vinylcarboxylic acid is 5% by weight or less.

However, the circumstances differ when the acrylic copolymer is used as a medical pressure-sensitive adhesive which is not contacted with a wounded portion.

The medical water-absorptive polymer of the present invention can be produced by copolymerizing the mixture of the above-described monomers by conventional copolymerization method.

The copolymerization methods which can be used are a solution polymerization method, an emulsion polymerization method, a suspension polymerization method, an a bulk polymerization method.

In the copolymerization method, for example, the solution polymerization is carried out by heat-stirring the monomer mixture in the presence of a solvent and a polymerization initiator. Examples of the solvent are methanol, ethanol, isopropanol, acetone, methyl ethyl ketone, methyl acetate, ethyl acetate, toluene, xylene, and an ethylene glycol alkyl ether. Those solvents can be used alone or as mixtures thereof. Examples of the polymerization initiator are benzoyl peroxide, cumene hydroperoxide, diisopropyl peroxydicarbonate, and azobisisobutyronitrile. Those polymerization initiators can be used alone or as mixtures thereof.

In the copolymerization method, the emulsion polymerization is carried out by heat-stirring a dispersion comprising water, a surfactant, a water-soluble polymerization initiator, and the monomer mixture.

Examples of the surfactant which can preferably be used are an anionic surfactant and a nonionic surfactant. Representative examples of the surfactant are sodium laurylsulfate, lauroylsarcosine sodium, polyoxyethylene lauryl ether, polyoxyethylene sorbitan monooleate, sorbitan sesquioleate, and a sucrose fatty acid ester. Those can be used alone or as mixtures thereof.

Examples of the water-soluble polymerization initiator are ammonium persulfate, potassium persulfate, hydrogen peroxide, and t-butyl hydroperoxide.

The present invention can also employ a photopolymerization.

The photopolymerization is carried out by irradiating the monomer mixture with ultraviolet (UV) rays in the presence of a photopolymerization initiator. Examples of the photopolymerization initiator are acetophenone photopolymerization initiators such as 4-phenoxydichloroacetophenone, 4-t-butyl-dichloroacetophenone, 4-t-butyl-trichloroacetophenone, diethoxyacetophenone, 2-hydroxy-2-methyl-1-phenylpropan-1-one, 1-(4-isopropylphenyl)-2-hydroxy-2-methylpropan-1-one, 1-(4-dodecylphenyl)-2-hydroxy-2-methylpropan-1-one, 4-(2-hydroxyethoxy)-phenyl-(2-hydroxy-2-propyl)ketone, 1-hydroxycyclohexylphenylketone, 2-methyl-1-[4-(methylthio)phenyl]-2-morpholinopropane-1, etc.; benzoin photopolymerization initiators such as benzoin, benzoin methyl ether, benzoin ethyl ether, benzoin propyl ether, benzoin butyl ether, benzyl dimethyl ketal, etc.; benzophenone photopolymerization initiators such as benzophenone, benzoylbenzoic acid, methyl benzoylbenzoate, 4 -phenylbenzophenone, hydroxybenzophenone, 4-benzoyl-4'-methyldiphenyl sulfide, 3,3'-dimethyl-4-methoxybenzophenone, etc.; and thioxanthone photopolymerization initiators such as thioxathone, 2-chlorothioxathone, 2-methylthioxathone, 2,4-dimethylthioxane, isopropylthioxathone, 2,4-dichlorothioxathone, 2,4-diethyloxathone, 2,4-diisopropylthioxathone, etc.

In this case, if necessary, a photopolymerization initiation assistant reagent may be added to the system. Examples of the photopolymerization initiation assistant are triethanolamine, methyldiethanolamine, triisopropanolamine, 4,4'-dimethylaminobenzophenone, 4,4'-diethylaminobenzophenone, ethyl 2-dimethylaminobenzoate, ethyl 4-dimethylaminobenzoate, (n-butoxy)ethyl 4-dimethylaminobenzoate, isoamyl 4-dimethylaminobenzoate, and 2-ethylhexyl 4-dimethylaminobenzoate. Those can be used alone or as mixtures thereof.

The amount of the photopolymerization initiator differs according to the extinction coefficient thereof, etc., but is preferably from 0.005 to 0.5 part by weight, and more preferably from 0.01 to 0.2 part by weight, per 100 parts by weight of the monomer mixture.

The photopolymerization is preferably carried out by a method of obtaining the copolymer by pre-irradiating the mixture of the monomers and the photopolymerization initiator with UV rays at a definite dosage after sufficiently replacing the inside atmosphere of the reaction vessel containing the mixture to obtain a partially polymerized syrup, coating the partially polymerized syrup or flow-casting the syrup in a frame, and then sufficiently irradiating the coated or flow-casted syrup with UV rays. The total irradiation doses at the partial polymerization are preferably from 20 to 300 mj/cm$^2$ and the total irradiation doses at the complete polymerization are preferably from 1,000 to 10,000 mJ/cm$^2$, and more preferably from 2,000 to 5,000 mJ/cm$^2$.

Furthermore, it is preferred that the medical water-absorptive polymer comprises an acrylic copolymer obtained by copolymerizing a mixture of the acrylic composition further compounded with from 0.01 to 1% by weight of a multifunctional acrylate or methacrylate to attain the above-described objects of the present invention.

That is, this medical water-absorptive polymer of the present invention is a water-absorptive polymer used for medical treatment and the water-absorptive polymer comprises an acrylic copolymer obtained by copolymerizing a mixture of from 60 to 80% by weight of the alkoxyalkyl acrylate, from 20 to 40% by weight of the N-vinyllactam, 10% by weight or less of the vinylcarboxylic acid, and from 0.01 to 1% by weight of a multifunctional acrylate or methacrylate.

In the acrylic copolymer described above, the amount of the alkoxyalkyl acrylate is from 60 to 80% by weight based on the total weight of the copolymer. If the amount of this component is less than 60% by weight, the flexibility of the copolymer film obtained is undesirably decreased and, on the other hand, if the amount thereof is over 80% by weight, the hydrophilic property of the copolymer film is undesirably decreased.

Further, in the acrylic copolymer described above, the amount of the N-vinyllactam is from 20 to 40% by weight based on the total weight of the copolymer. If the amount of this component is less than 20% by weight, the hydrophilic property of the copolymer film obtained is undesirably decreased and, on the other hand, if the amount thereof is over 40% by weight, the water solubility of the acrylic copolymer formed is undesirably increased, whereby the acrylic copolymer is dissolved in moisture or a body fluid to form a stream.

Furthermore, in the acrylic copolymer, the amount of the vinylcarboxylic acid is 10% by weight or less based on the total weight of the copolymer. That is, the amount of the vinylcarboxylic acid used is from 0 to 10% by weight, and preferably from 0 to 5% by weight, based on the total weight of the copolymer. If the amount of this component is over 10% by weight, the water-absorbability of the copolymer film obtained is undesirably accelerated to cause a possibility to decrease the wound healing ability.

In the present invention, the reason for compounding the vinylcarboxylic acid is to further improve the water-absorbability. If the amount thereof is over 10% by weight, the stanching property of the copolymer film obtained is decreased to cause the possibility to delay the wound treatment. Thus, by the reason described above, it is preferred that the amount of the vinylcarboxylic acid is 5% by weight or less.

However, the circumstances differ when the acrylic copolymer is used as a medical pressure-sensitive adhesive which is not contacted with a wounded portion.

The amount of the multifunctional acrylate or methacrylate used in the acrylic copolymer is from 0.01 to 1% by weight based on the total weight of the copolymer. If the amount of this component is less than 0.01% by weight, the crosslinking is undesirably insufficient, whereby the strength of the copolymer is decreased and the copolymer becomes water-soluble. On the other hand, if the amount thereof is over 1% by weight, the flexibility and the pressure-sensitive adhesive property of the copolymer film obtained are decreased, the hydrophilic property of the copolymer is greatly decreased, and the copolymer film is whitened, which are undesirable in the present invention.

The water-absorptive polymer of the present invention is an acrylic copolymer obtained by copolymerizing the acrylic composition further compounded with a multifunctional acrylate or methacrylate. Hence, the materials described above for the acrylic copolymer which does not contain the multifunctional acrylate or methacrylate can be used as the alkoxyalkyl acrylate, the N-vinyllactam, and the vinylcarboxylic acid in the acrylic composition.

Examples of the multifunctional acrylate or methacrylate used in the present invention are alkyl-type diacrylates or dimethacrylates, such as 1,4-butanediol diacrylate, 1,4-butanediol dimethacrylate, neopentyl glycol diacrylate, 1,6-hexanediol diacrylate, 1,6-hexanediol dimethacrylate, etc.; alkylene glycol-type diacrylates or dimethacrylates, such as diethylene glycol diacrylate, diethylene glycol dimethacrylate, triethylene glycol diacrylate, diethylene glycol dimethacrylate, polyethylene glycol 200 diacrylate, polyethylene glycol 400 diacrylate, polyethylene glycol 600 diacrylate, polyethylene glycol 200 dimethacrylate, polyethylene glycol 400 dimethacrylate, polyethylene glycol 600 dimethacrylate, polyethylene glycol 1000 dimethacrylate, polypropylene glycol 400 diacrylate, polypropylene glycol 400 dimethacrylate, etc.; ester-type diacrylates or dimethacrylates, such as hydroxypivalic acid neopentyl glycol diacrylate, etc.; trimethylolpropane-type tri- and tetra-acrylates or tri-methacrylates, such as trimethylolpropane triacrylate, trimethylolpropane trimethacrylate, ethoxylated trimethylolpropane triacrylate, ditrimethylolpropane tetraacrylate, etc.; pentaerythritol-type tri- and tetra-acrylates or tri- and tetra-methacrylates, such as pentaerythritol triacrylate, pentaerythritol tetramethacrylate, etc.; isocyanurate-type triacrylates or trimethacrylates, such as tris(acryloxyethyl) isocyanurate, tris(methacryloxyethyl) isocyanurate, etc.; and bisphenol A-type diacrylates or dimethacrylates, such as ethoxylated bisphenol A diacrylate, ethoxylated bisphenol A dimethacrylate, etc.

From the points of the hydrophilic property and the safety, the alkylene glycol-type diacrylates or dimethacrylates are preferred and polyethylene glycol 600 dimethacrylate is more preferred.

The medical water-absorptive polymer of the present invention can be produced by copolymerizing the mixture of the monomers described above by the above-described polymerization method.

Practically, the medical water-absorptive polymer can be produced by copolymerizing the mixture of the above-described monomers and a plasticizer by a bulk polymerization, a solution polymerization, a UV polymerization, etc.

In the polymerization method, for example, the UV polymerization can be carried out by irradiating the mixture of the monomers and the plasticizer with a sufficient dosage of UV rays in the presence of the photopolymerization initiator, or by pre-irradiating the monomer mixture excluding the polyfunctional acrylate or methacrylate with a definite dosage of UV rays in the presence of a photopolymerization initiator to obtain a partially polymerized syrup and then after adding thereto the multifunctional acrylate or methacrylate and the plasticizer, irradiating the resulting mixture with a sufficient dosage of UV rays.

In this case, the amount of the photopolymerization initiator differs according to the extinction coefficient thereof, etc., but is preferably from 0.005 to 0.5 part by weight, and more preferably from 0.01 to 0.2 part by weight, per 100 parts by weight of the monomers.

The photopolymerization is preferably carried out by a method of obtaining the copolymer containing the plasticizer, wherein after sufficiently replacing the inside atmosphere of a reaction vessel containing the mixture of the monomers and the plasticizer excluding the multifunctional acrylate or methacrylate with nitrogen, the mixture is pre-irradiated with a definite dosage of UV rays to obtain a partially polymerized syrup, and after coating a mixture of the partially polymerized syrup, the multifunctional acrylate or methacrylate, and, if necessary the plasticizer as described below or flow-casting the mixture in a frame, the coated or flow-casted mixture is irradiated with sufficient UV rays, or after sufficiently replacing the inside atmosphere of a reaction vessel containing the mixture of the monomers, the plasticizer, and the photopolymerization initiator with nitrogen, the mixture is irradiated with a definite dosage of UV rays to obtain a partially polymerized syrup, and after coating the partially polymerized syrup obtained or flow-casting the syrup in a frame, the coated or flow-casted mixture is irradiated with sufficient UV rays.

In this case, the total irradiation doses at the partial polymerization are preferably from 20 to 300 mJ/cm$^2$ and the total irradiation doses at the complete polymerization are preferably from 1,000 to 10,000 mJ/cm$^2$ and more preferably from 2,000 to 5,000 mJ/cm$^2$.

The medical water-absorptive polymer of the present invention also includes the water-absorptive polymer obtained by crosslinking the mixture of at least 60% by weight of the acrylic copolymer and 40% by weight or less of the plasticizer as described below.

In the present invention, the term "at least 60% by weight of the acrylic copolymer" includes the polymer consisting of the acrylic copolymer, that is, the polymer containing 100% by weight of the acrylic copolymer, and there is a case that it is necessary to realize insolubilization of the acrylic copolymer and realize the shape-retention property.

In compounding the acrylic copolymer with the plasticizer, if the amount of the plasticizer compounded is over 40% by weight based on the total weight of the acrylic copolymer and the plasticizer, the characteristics of the acrylic copolymer are lost, the insolubilization by the radiations such as electron rays, etc., and with a chemical crosslinking agent, which will be described after becomes difficult, or also the insolubilization with the polyfunctional acrylate or methacrylate becomes difficult, which is undesirable in the present invention. Thus, from those standpoints, the amount of the plasticizer compounded is preferably 30% by weight or less.

The insolubilization is a crosslinking by irradiation with radiations such as electron rays, γ-rays, etc. In this case, the dosage of the irradiation of the radiation differs according to the extent of the water-solubility of the acrylic copolymer but is preferably 50 kGy or less. If the irradiation dosage is at least 25 kGy, it also functions as the sterilization defined by the medical treatment-related laws and regulations but if the dosage is over 50 kGy, the occurrence of a denaturation such as coloring, etc., is severe and thus irradiation is restricted.

In the present invention, the flexibility and the pressure-sensitive adhesive property of the medical water-absorptive polymer can be more improved by adding the plasticizer to the acrylic copolymer. The plasticizer which is preferably used is a compound having a good compatibility with the acrylic copolymer and a hydrophilic property.

Specific examples of the plasticizer used in the present invention are low molecular weight polyhydric alcohols such as ethylene glycol, diethylene glycol, triethylene glycol, propylene glycol, dipropylene glycol, glycerol, diglycerol, 2,3-butanediol, 1,2-butanediol, 3-methyl-1,3-butanediol, 3-methyl-1,3,5-pentanetriol, 2-ethyl-1,2-hexanediol, etc.; polyethylene glycol, polypropylene glycol, polyoxyethylene butyl ether, polyoxyethylene, polyoxypropylene, polyoxypropylene glyceryl ether, polyoxypropylene sorbitol, and polyoxyethylene polyoxypropylene pentaerythritol ether each having an average molecular weight of 1,000 or less. Of these compounds, polyoxypropylene glyceryl ether having an average molecular weight of from 200 to 800, polyoxypropylene glycol having an average molecular weight of from 200 to 800, and polyoxypropylene sorbitol having an average molecular weight of from 200 to 800 are particularly preferred.

The reason for compounding the plasticizer is to more improve the flexibility and the pressure-sensitive adhesive property of the acrylic copolymer and for the reason, it is preferred that the amount of the plasticizer compounded is 30% by weight or less.

When the water solubility of the acrylic copolymer is increased by compounding therewith the plasticizer, the insolubilization by crosslinking by irradiation with radiations such as electron rays, γ-rays, etc., and the crosslinking method and the crosslinking condition are same as the case described above.

In the medical water-absorptive polymer of the present invention, it is preferred that the acrylic copolymer (including the crosslinked copolymer) obtained by the method described above or the plasticizer-containing acrylic copolymer (including the crosslinked copolymer) obtained by the method described above has a 50% modulus of from 1 to 50 g/mm$^2$ and a water absorption of from 100 to 5,000%, and preferably from 300 to 3,000%, for the reason described hereinafter.

The medical water-absorptive polymer of the present invention having a 50% modulus of from 1 to 50 g/mm$^2$ has a flexibility and an elongation, and the film of the polymer does not give a feeling of incongruity to a skin, shows a good adhesive property onto a skin, and can keep the adhesive property at bending portions such as an elbow, a knee, etc., following the hard movement.

In the medical water-absorptive polymer of the present invention, if the 50% modulus is over 50 g/mm$^2$, the polymer increases the hardness to lose the elongation property and the film thereof gives a feeling of incongruity to a skin to cause a physical stimulation and also decreases the adhesive property to bending portions such as an elbow, a knee, etc. On the other hand, if the 50% modulus is less than 1 g/mm$^2$, the strength of the polymer is insufficient, whereby the polymer cannot endure for a practical use.

Further, in the medical water-absorptive polymer of the present invention, it is particularly preferred that the 24 hour water absorption is from 100 to 5,000%.

The medical water-absorptive polymer of the present invention is adhered to a wounded portion, etc., of the cuticle, swells by absorbing the exudate from the wounded portion, etc., and becomes a gel state. That is, when the medical water-absorptive polymer of the present invention is contacted with body tissue fluid such as a sweat, a tear, urine, a serum, an exudate from a wounded portion, etc., the polymer gradually absorbs the fluid to form a water-containing gel. In this case, the fluid absorbed by the polymer is strongly retained in the polymer and the fluid does not easily ooze therefrom by mechanical pressure.

With the increase of the water absorption, the flexibility and a stress relaxation are increased but when the water absorption is over 5,000%, the gel strength is decreased and the polymer becomes brittle or the polymer tends to be dissolved, whereby the polymer becomes substantially unusable. However, when the water absorption is not higher than 5,000%, a gel state having a substantially usable strength can be obtained and in particular, when the water absorption is 3,000% or less, a gel state having an effectively usable strength can be obtained.

On the other hand, when the water absorption is less than 100%, if the polymer film is adhered to a normal skin, a maceration by a sweat occurs, whereby a skin stimulation such as rash, etc., is liable to occur or if the polymer film is adhered to a wounded skin, an exudate excessively remains on the surface of the skin or an exudate oozes to the outside of the film, which gives an inconvenient influence on the treatment of the wound. To the contrary, if the water absorption is at least 100%, the occurrence of the above-described disadvantages is prevented and in particular, if the water absorption is at least 300%, the occurrence of the disadvantages is remarkably prevented.

The water absorption in the present invention is as follows. The medical water-absorptive polymer is formed into a film or a sheet, the film or the sheet is cut into an area of 1.5 cm × 1.5 cm, and after measuring the weight thereof before absorbing water, each cut piece is immersed in 135 ml of a phosphoric buffer isotonic sodium chloride solution (pH 7.4) at 32° C. for 24 hours. Each cut piece was then took out from the solution, water on the surfaces was wiped off, and the weight thereof after absorbing the solution is measured. The water absorption is the value calculated from the increased weight.

The medical water-absorptive polymer of the present invention may be used in a state of previously containing water within the substantially usable range. Examples of the water which can be used are distilled water, distilled water for injection, sterilized purified water, an isotonic sodium chloride solution, phosphoric acid buffer isotonic sodium chloride solution, etc. Each water or solution may further contain a drug or drugs.

The drugs which can be contained in water which is previously contained in the medical water-absorptive polymer of the present invention are not particularly restricted, and examples thereof are antibacterial agents such as povidone iodine, iodine, sulfadiazine, silver sulfadiazine, benzalkonium chloride, cetalkonium chloride, methylbenzethonium, neomycin sulfate, hexachlorophene, Eosine, penicillin G, cefalocin, cefaloridine, tetracycline, lincomycin, nystatin, kanamycin, penicillinase resistant penicillin, fradiomycin sulfate, silver lactate, etc.; salicylic acid esters as physiologically active materials; drugs for cataplasm, such as menthol, camphor, peppermint, a capsicum extract, capsaicin, etc.; steroid drugs such as predonizolon, dexamethasone, hydrocortisone, etc.; non-steroid drugs such as indomethacin, ketoprofene, dichlofenac, ibuprofen, etc.; angina pectoris terapeutical drugs such as nitroglycerin, isosorbid dinitrate, etc.; local anesthesias such as benzocaine, procaine, xylocaine, etc.; anti-histamic agents such as diphenhydramine, etc.; $\beta$-blockers such as alprenol, propranol, pindolol, etc.; antihypotensive agents such as clonidine, nifedipine, etc.; bronchodilator agents such as methylephedrine, clonaprenalin, salbutamol, terbutamine, etc.; drugs for asthma, such as cromoglicic acid, etc.; immuno-controlling cyclosporin A; prostaglandins such as $PGE_1$, $PGE_2$, $PGI_2$, etc., and the derivatives thereof; growth factor hormones such as TGF, FGF, PDGF, EGF, etc.; water-soluble collagens; hyaluronic acid; chondroitin sulfuric acid; an aloes extract; a snake gourd extract; various kinds of vitamins; eicosapentaenic acid and the derivartives thereof; and Chinese traditional medicines such as Ligusticum acutilobum S et Z, Lithospermum erythrorhizon, etc. Those can be used alone or as mixtures thereof.

The medical water-absorptive polymer swells on absorbing water and becomes a gel state, which can provide a suitable wet environment for wet healing of a skin wound. That is, a dressing for wound having excellent water-absorptive property, the skin adhesive property, the flexibility, and the transparency, which are the main characteristics for the pharmaceutical preparation necessary for the wet healing, is provided.

Examples of the dressing for wound are a film or a sheet formed using the medical water-absorptive polymer, the film or the sheet of the medical water-absorptive polymer, which is further physically or chemically crosslinked, the film or the sheet of the medical water-absorptive polymer, which is dried, etc.

The dressing for wound of the present invention have various forms according to the use but the film-form or sheet-form dressing for wound as described above has a high general usability and there are films or sheets of the medical water-absorptive polymer and mesh-form or porous films or sheets of the polymer.

In other words, in the present invention, the film-form or sheet-form dressing for wound formed using the medical water-absorptive polymer may not have holes or may be porous, that is, may have holes.

The thickness of the film-form or sheet-form dressing for wound is usually at least 10 $\mu$m, preferably from 75 to 5,000 $\mu$m, more preferably from 100 to 2,000 $\mu$m, and most preferably from 200 to 1,000 $\mu$m. If the thickness thereof is less than 10 $\mu$m, a cutting phenomenon of the film frequently occurs undesirably and if the thickness is over 5,000 $\mu$m, feeling of using such a thin dressing for wound is poor and also it is meaningless to employ such a large thickness.

Since the medical water-absorptive polymer of the present invention has an excellent thermoplasticity, the polymer can be formed into a sheet form by extrusion molding. Any conventional methods such as inflation molding, T-die molding, lamination molding, etc., can be used as the extrusion molding, and since a high-temperature extrusion and quick cooling are applicable, the film or sheet of the polymer having an excellent optical property can be obtained. Furthermore, from the standpoints that the production speed can be increased due to the good cooling efficiency and the thickness of the sheet formed can be easily controlled, T-die molding is preferably employed.

In addition, a single screw extruder or a twin screw extruder can be used as the extruder.

By properly controlling the molding conditions such as the molding temperature, the die lip width, the extrusion speed, the drawing speed, etc., the thickness of the film or sheet can be controlled.

In this case, the molding temperature is preferably from 140° C. to 180° C., and more preferably from 150° C. to 170° C. If the molding temperature is lower than 140° C., non-melting materials frequently enter the molded product to cause a possibility of giving scattering to the quality of the products. On the other hand, if the molding temperature is higher than 180° C., the phenomena of film cutting and entrance of bubbles undesirably occur.

Any conventional methods such as a calender method, a casting method, an extrusion method, etc., can be used as the film-forming method of the film or the sheet of the medical water-absorptive material of the present invention. However, when the polymerization method for producing the medical water-absorptive polymer is a photopolymerization, the monomer mixture containing the photopolymerization initiator or the partially polymerized syrup thereof, or the monomer mixture containing the photopolymerization initiator and the plasticizer or the partially polymerized syrup thereof is coated by a flow-casting method on a releasable film comprising a polyester film, etc., at a definite thickness and after covering the coated layer with a transparent releasable film, the coated layer is sufficiently irradiated with UV rays in an inert gas atmosphere, whereby the polymerization and the film formation are simultaneously conducted.

The film or the sheet-thus obtained is cut into a desired form and can be used as a dressing for wound.

In this case, the dressing in a mesh form or a porous form is also useful.

The mesh-form dressing can be obtained by punching the film or sheet with a mold or by molding in a casting method with a mesh-form mold. Also, the porous dressing can be obtained by swelling the film or the sheet by absorbing water and then dry freezing the swelled film or sheet.

The mesh-form and porous dressings have excellent gas permeability and flexibility, and are advantageous in the cost for raw materials.

In the present invention, the dressing for wound in which the strength, the fixing property, the form-retention property, the adhesive property, etc., are improved by covering one surface of the film or sheet or the mesh-form or porous film or sheet with a backing material is also useful.

In this case, the size of the backing material is same as or larger than the size of each dressing of each form. Any conventional materials can be used as the material of the backing material. Specific examples of the material for the backing material are papers, nonwoven fabrics, cotton fabrics, synthetic resin fabrics, synthetic resin films, synthetic resin foams, mesh-form or network papers, nonwoven fabrics, cotton fabrics, synthetic resin fabrics, or synthetic resin films, and the surgical tapes, the medical pressure-sensitive adhesive sheets, pressure-sensitive adhesive dressings, etc., using the above films or sheets as a substrate. Of those, the materials having excellent gas permeability and moisture permeability are more preferred.

In the present invention, by irradiating the film-form or sheet-form dressing for wound thus formed with radiations such as γ-rays, electron rays, etc., crosslinking can be applied thereto. The irradiation dosage of the radiation is preferably from 5 to 50 kGy and if the dosage is 25 kGy or higher, the irradiation also functions as the sterilization defined by the medical treatment-related laws and regulation. However, if the dosage is over 50 kGy, the occurrence of denaturation such as coloring is remarkable and the use thereof is restricted.

In the present invention, by radical polymerizing the mixture of the monomers, the solvent, and the polymerization initiator in the conventional operation, an acrylic copolymer can be obtained and by casting the solution of the acrylic copolymer, a film is formed. The thickness of the film is controlled to be from 10 to 75 $\mu$m, and preferably from 20 to 50 $\mu$m. If the thickness is over 75 $\mu$m, impurities and the residual monomers cannot be sufficiently removed and also the copolymer is greatly foamed at drying described below, which are undesirable. On the other hand, if the thickness is less than 10 $\mu$m, the water absorbing amount is reduced and the desired strength is not obtained, which are also undesirable in the present invention.

By drying the film obtained under a definite condition, the film-form dressing for wound from which the solvent, etc., (i.e., the solvent and/or prepolymers; hereinafter referred to as "impurities") and the residual monomers are removed can be obtained.

In this case, the drying condition differs according to the thickness of the film and further the drying method such as a vacuum drying, or a normal-pressure drying. For example, in normal pressure drying, when the thickness of the film is from 10 to 75 $\mu$m, it is preferred that the drying condition is from 30 seconds to 20 minutes at a temperature of 110° to 115° C. and particularly from 1 to 15 minutes at a temperature of from 120° C. to 140° C.

More practically, under, for example, a sufficient air current, when the thickness of the film is not larger than 25 $\mu$m, it is preferred that the drying condition is for at least 2 minutes at 130° C., and particularly for about 3 minutes at 130° C. and when the thickness of the film is from 25 to 50 $\mu$m, it is preferred that the drying condition is for at least 5 minutes at 130° C., and particularly for about 7 minutes at 130° C. Furthermore, when the thickness of the film is from 50 to 70 $\mu$m, it is preferred that the drying condition is for at least 10 minutes at 130° C., and particularly for about 12 minutes at 130° C.

Thus, the drying time can be changed in accordance with the drying temperature but the drying temperature over 150° C. is undesirable since skinning occurs on the surface of the film, whereby impurities and the residual monomers cannot be sufficiently removed and also possibility occurs to cause severe foaming. Also, the drying temperature of 110° C. or less is undesirable since it takes a long time to remove impurities and the residual monomers and further there is a possibility of not sufficiently removing them.

As a result of removing the impurities and the residual monomers form the film (dressing) formed by the medical water-absorptive polymer by drying the film under the suitable drying condition, the quality of the film is improved and also bad influences onto a body cue to the impurities and the residual monomers can be removed, whereby the safety of the dressing for wound is improved.

When the dressing for wound contains drug(s) at drying, it is necessary to sufficiently consider the decomposition, etc., of the drug(s) by heating.

In the dressing for wound of the present invention, the dressing having a hole-having pressure-sensitive adhesive layer (hereinafter referred to as "porous pressure-sensitive adhesive") formed on the surface of the adhering side thereof to a wound is very useful for the following reason.

That is, by forming the porous pressure-sensitive adhesive layer on the surface of the adhesive side of the dressing to a wound, the adhesive property to the surface of the wound portion is improved to increase the sealing property and an exudate is efficiently absorbed through the holes. In this case, if desired, a crosslinking treatment is applied to the dressing having the porous pressure-sensitive adhesive layer.

The porous pressure-sensitive adhesive layer can be obtained by punching the coated film of a pressure-sensitive adhesive used for medical treatments (hereinafter referred to as a "medical pressure-sensitive adhesive") at a definite porosity.

Examples of the medical pressure-sensitive adhesive are acrylic pressure-sensitive adhesives such as an acrylic acid ester copolymer, etc.; acrylic oily gel pressure-sensitive adhesives obtained by adding compatible liquid component(s) to the acrylic pressure-sensitive adhesives; and rubbery pressure-sensitive adhesives such as a natural rubber, a polyisoprene rubber, a styrene-butadiene rubber, a polyisobutylene rubber, a styrene-butadiene-styrene copolymer, and those obtained by adding a tackifier (e.g., rosin, a rosin derivative, a terpene resin, an aliphatic hydrocarbon resin, and an aromatic petroleum resin), a reinforcing agent, a filler, etc., to the rubbery pressure-sensitive adhesives. In these medical pressure-sensitive adhesives, the acrylic pressure-sensitive adhesives and the acrylic oily gel pressure-sensitive adhesives giving small skin stimulation are preferred and in particular, the pressure-sensitive adhesives having a high moisture permeability are more preferably used.

The thickness of the porous pressure-sensitive adhesive layer is preferably from 5 to 100 $\mu$m, and more preferably from 10 to 50 $\mu$m. If the thickness thereof is less than 5 $\mu$m, there is an undesirable possibility that the adhesive property becomes insufficient and on the other hand, if the thickness is over 100 $\mu$m, there are undesirable possibilities that the adhesive property becomes excessive and also the holes are closed by the press-deformation of the pressure-sensitive adhesive layer.

The holes may be formed by any desired method but a punching roll is preferably used. The form of the holes may be any desired form, such as a circle, a regular square, etc., but the porosity per unit area of the pressure-sensitive adhesive layer is preferably from 5 to 75%, and more preferably from 10 to 30%. If the porosity is less than 5%, a suffucient moisture permeability is not undesirably obtained and on the other hand, if the porosity is over 75%, the sufficient sealing property and adhesive property are not undesirably obtained.

In the present invention, if necessary, the porous pressure-sensitive adhesive layer may contain drug(s) and the above-described drugs can be used as the drugs.

The dressing for wound of the present invention is prepared by adhering the porous pressure-sensitive adhesive layer to one surface of the film or the sheet of the medical water-absorptive polymer or by adhering the porous water-absorptive layer to one surface of the film or sheet obtained by extrusion-molding the medical water-absorptive polymer.

The dressing for wound of the present invention can also be obtained by adhering the porous pressure-sensitive adhesive layer to one surface of the film or the sheet of the medical water-absorptive polymer as described above and then irradiating the assembly with a radiation, or by irradiating the film or the sheet of the medical water-absorptive polymer with a radiation or irradiating the film or the sheet formed by extrusion molding the medical water-absorptive polymer with a radiation and then adhering the porous pressure-sensitive adhesive layer to the film or the sheet.

In the dressing for wound, the exudate from a wounded portion passes through the voids of the porous pressure-sensitive adhesive layer and reaches the water-absorptive polymer layer, whereby the exudate is gradually absorbed by the polymer to form a hydrogel. Since a part of water retained therein gradually evaporates off and the accumulation of the exudate is restricted, whereby a wet environment suitable for healing of the wound is maintained. Also, the porous pressure-sensitive layer, which is in contact with a normal skin surrounding the wound, shows an excellent adhesive property, whereby a sufficient sealing property for preventing the infection of bacteria is obtained.

On the other hand, in the dressing for wound, since the sweat in the adhered portion thereof passes through the voids of the porous pressure-sensitive adhesive layer, reaches the water-absorptive polymer layer, and is quickly absorbed by the polymer, the occurrences of the maceration and an inflammation caused thereby and decrease in the adhesive force can be prevented.

In the present invention, by forming a backing material on the opposite side of the dressing for wound having the porous pressure-sensitive adhesive layer to the side of the porous pressure-sensitive adhesive layer, the strength, the fixing property, the form-retention property, the adhesive property, etc., of the dressing for wound are improved, which are useful.

The dressing for wound of the present invention can be used for healing of skin wounds such as a dermal burn, a partial thickness wound, an incised wound, a sore, a suturus wound, a contused wound, a dermal ulcer, etc.

Furthermore, in the present invention, a medical bandage using the medical water-absorptive polymer is useful.

That is, the medical bandage of the present invention has an adhesive property to a wounded portion, etc., of a skin and a proper pressure-sensitive adhesive property is obtained by controlling the monomer composition of the acrylic copolymer or the amount of the plasticizer. Hence the medical bandage has excellent moisture absorption and the moisture permeability capable of preventing the occurrences of the maceration and the inflammation caused thereby, which frequently occur at a much sweat portion, etc.

Examples of the medical bandage are the film or the sheet of the medical water-absorptive polymer, the film or the sheet which is further physically or chemically crosslinked; the film or the sheet formed using the medical water-absorptive polymer followed by drying; these medical bandages each having the porous pressure-sensitive adhesive layer formed on the surface of the side adhered to a wounded portion; and these medical bandages each having a backing material formed on the opposite side thereof to the porous pressure-sensitive adhesive layer side.

In this case, the film or the sheet formed using the medical water-absorptive polymer, the crosslinking method and the drying method thereof, the film or sheet having the porous pressure-sensitive adhesive layer formed thereon, the porous pressure-sensitive adhesive layer, the production method and the forming method of them, the backing material, etc., are same as the above-described case and hence the explantions of them are omitted.

Of those medical bandages, the bandage comprising the film or the sheet formed using the-medical water-absorptive polymer having formed thereon the backing material is preferable and in this case, the medical bandage wherein the thickness of the film or the sheet is from 10 µm to 1 mm, and preferably from 30 to 500 µm is preferable since such a bandage has the improved strength, fixing property, form-retention property, adhesive property, etc., and also shows good feeling of use.

The process of producing the medical water-absorptive polymer of the present invention is a process of producing a water-absorptive polymer used for medical treatment for attaining the above-described objects and the water-absorptive polymer is produced by copolymerizing an acrylic composition comprising from 60 to 80% by weight of an alkoxyalkyl acrylate, from 20 to 40% by weight of an N-vinyllactam, and 10% by weight or less of a vinylcarboxylic acid, casting the copolymerization product, and drying the casted copolymer to remove the residual monomers and volatile impurities.

The alkoxyalkyl acrylate, the N-vinyllactam, and the vinylcarboxylic acid used in the process of the present invention for producing the medical water-absorptive polymer and the concentrations of them are same as those described above and hence their explanations are omitted.

The feature of the production process in the present invention is that the acrylic composition described above is copolymerized and after casting the copolymerization product, the casted copolymer is dried to remove the residual monomers and volatile impurities.

The residual monomers are monomers remaining after the copolymerization and the impurities are, for example, a solvent and prepolymers. By removing these monomers and impurities, a medical water-absorptive polymer having a more stable quality is obtained.

In the production process of the present invention, by copolymerizing the specific acrylic composition and then removing the residual monomers and the impurities, the medical water-absorptive polymer of the present invention having a more excellent quality is obtained as described above. The medical water-absorptive polymer obtained by the process of the present invention has the features that the polymer has excellent water absorbing property, flexibility, and transparency, and also the contents of the residual monomers and impurities are less than the case of producing by a UV polymerization method.

Using the medical water-absorptive polymer obtained by the production process of the present invention, the dressing for wound and the medical bandage of the present invention can be obtained by the manners described above.

In this case, the production process of the dressing for wound of the present invention by extrusion-molding the medical water-absorptive polymer obtained to form a sheet and then applying a crosslinking treatment thereto is useful since the dressing for wound having an excellent quality is obtained by this process.

The production process of the medical bandage of the present invention by extrusion-molding the medical water-absorptive polymer obtained to form a sheet and then applying a crosslinking treatment thereto is also useful since the medical bandage having an excellent quality is obtained by this process.

If desried, by incorporating a drug into the paste (the water-absorptive polymer) layer of the medical bandage of the present invention, the bandage can be used as a transdermal drug delivery patch.

In particular, the dressing for wound of the present invention has preferably a bacteria permeation resistance and also the medical bandage having an excellent moisture permeability is preferably used.

In addition, the backing material can be introduced before or after the irradiation with a radiation but from the point of retaining a sterilized state, the backing material is preferably introduced before the irradiation with a radiation.

Also, by enclosing each dressing for wound or each medical bandage of the present invention in a bacteria-intercepting package, etc., in a sterilized state, they can take a form of retaining the sterilized state. In addition, an EOG method, an electron ray method, or a γ-ray method is preferably used as the sterilizing method.

That is, by making the form capable of retaining a sterilized state by enclosing each dressing for wound or each medical bandage in the bacteria-intercepting package, and then applying thereto a crosslinking treatment and a sterilizing treatment by the irradiation with electron rays or γ-rays, the dressing for wound and the medical bandage using the medical water-absorptive polymer of the present invention can be circulated as commercial products.

In this case, the dosage of the radiations such as electron rays, γ-rays, etc., differs according to the hydrophilic extent of the medical water-absorptive polymer but is preferably 50 kGy or less. If the dosage is at least 25 kGy, it can also function as the sterilization defined by the meical treatment-related laws and regulations but if the dosage is over 50 kGy, the occurrence of the discoloration such as coloring, etc., is severe and the use thereof is restricted.

In the medical water-absorptive polymer, it is preferred that the 50% modulus thereof is from 1 to 50 g/mm$^2$ and the water absorption is from 100 to 5,000%, and particularly from 300 to 3,000%.

The dressing for wound of the present invention has excellent water absorptive property, sealing property, skin adhesive property, flexibility, and transparency, can provide a suitable wet environment for wet healing of skin wounds, and can be used to heal a skin wound such as a dermal burn, a partial thickness wound, an incised wound, a contused wound, a sore, a suturus wound, a dermal ulcer, etc.

Also, the medical bandage of the present invention has excellent skin adhesive property, water absorptive property, and moisture permeability capable of preventing the occurrences of stuffiness and the inflammation caused thereby, which frequently occur at much sweat portions, etc., and can be used as fixing surgical tapes, medical pressure-sensitive adhesive sheets used for an urgent plaster, a magnetic plaster, etc., a pressure-sensitive adhesive bandages having an elasticity, transdermal drug delivery patch preparations, etc.

The medical water-absorptive polymer of the present invention has the construction described above, has an excellent water-absorptive property since the hydrophilic acrylic copolymer or the acrylic copolymer added with the plasticizer therefor is properly crosslinked or becomes water-swellable and is insolubilized without being crosslinked, and also since the medical water-absorptive polymer is an acrylic copolymer having a low glass transition point or the acrylic copolymer added with the plasticizer therefor, the polymer of the present invention has functions excellent in the flexibility and the skin adhesive property.

Also, since the medical water-absorptive polymer of the present invention is an acrylic copolymer, the polymer of the present invention has excellent transparency. That is, the medical water-absorptive polymer of the present invention can simultaneously satisfy the water absorptive property, the skin adhesive property, the flexibility, and the transparency which have never been simultaneously satisfied by conventional dressings for wound and medical bandages used for wet healing, and has a function to show an excellent healing ability.

Furthermore, when in the medical water-absorptive polymer of the present invention, the hydrophilic acrylic mixture containing the plasticizer is properly crosslinked with the multifunctional acrylate or methacrylate, the water-swelling property of the polymer is insured and the polymer is insolubilized by the crosslinking, whereby the polymer of the present invention can have an excellent water-absorptive property. Also, since the hydrophilic acrylic mixture constituting the medical water-absorptive polymer of the present invention is an acrylic mixture having a low glass transition point, the medical water-absorptive polymer has a function excellent in the flexibility and the skin adhesive property.

In this case, since the polymer comprises the acrylic copolymer or mixture, the medical water-absorptive polymer of the present invention has excellent transparency. That is, medical water-absorptive polymer of the present invention can simultaneously satisfy the water absorptive property, the skin adhesive property, the flexibility, and the transparency which have never been satisfied by conventional dressing for wound used for wet healing, and thus has a function to expect an excellent healing ability.

The present invention is described in more detail by reference to the following examples but the invention is not limited thereby.

EXAMPLE 1

In a closed-type reaction vessel equipped with a stirrer were placed 0.05 part by weight of 1-(4-isopropylphenyl)-2-hydroxy-2-methylpropan-1-one, 56 parts by weight of 2-methoxyethyl acrylate, and 24 parts of N-vinyl-2-pyrrolidone. After replacing the inside atmosphere of the reaction vessel with a nitrogen gas at a flow rate of 10 ml/minute for 2 hours, the mixture was irradiated with UV rays at total doses of about 50 mj/cm$^2$ to obtain a partially photopolymerized syrup.

To the syrup was added 20 parts by weight of polyoxypropylene glyceryl ether having an average molecular weight of 400 and the resulting mixture was stirred for one hour under a nitrogen gas stream. The product obtained was flow-cast in a silicone-made frame having a thickness of 1.2 mm disposed on a releasable PET film subjected to a silicone treatment and after covering thereon with a similar releasable PET film, the assembly was uniformly irradiated from both sides thereof with UV rays such that the total dose became 3,000 mj/cm$^2$ while properly air-cooling in an inert atmosphere. After drying the flow-cast film at 130° C. for 30 minutes, the film was irradiated with γ-rays at a dose of 25 kGy to obtain a dressing for wound of the present invention as a transparent sheet having a thickness of 1 mm. The 50% modulus thereof was 4.9 g/mm$^2$ and the water absorption thereof was 1,240%.

EXAMPLE 2

In a closed-type reaction vessel equipped with a stirrer were placed 0.2 part by weight of azobisisobutyronitrile, 80 parts by weight of 2-methoxyethyl acrylate, 20 parts by weight of N-vinyl-2-pyrrolidone, and 150 parts by weight of toluene. After replacing the inside atmosphere of the reaction vessel with a nitrogen gas at a flow rate of 10 ml/minute for 2 hours, the mixture was stirred for 9 hours while keeping the inside temperature of the reaction vessel at a temperature of from 60° C. to 62° C.

83.3 Parts by weight of toluene was added to the reaction mixture followed by stirring at 70° C. for 2 hours to complete the reaction. The reaction product was cooled to room temperature to obtain a solution of the medical water-absorptive polymer (acrylic copolymer) of the present invention.

The solution of the medical water-absorptive polymer (acrylic copolymer) was coated on a releasable paper at a definite thickness and dried at 130° C. for 5 minutes, whereby the solvent and the unreacted monomers were removed and a transparent film having a thickness of 90 μm was obtained.

Furthermore, by irradiating the film with γ-rays at a dose of 25 kGy, the dressing for wound of the present invention was obtained. The 50% modulus of the dressing for wound was 12.5 g/mm$^2$ and the water absorption thereof was 490%.

EXAMPLE 3

By following the same procedure as in Example 2 except that the monomer composition was 70 parts by weight of 2-methoxyethyl acrylate and 30 parts by weight of N-vinyl-2-pyrrolidone, the dressing for wound of the present invention was obtained. The 50% modulus thereof was 20.0 g/mm$^2$ and the water absorption was 1,100%.

EXAMPLE 4

By following the same procedure as in Example 2 except that the monomer composition was 65 parts by weight of 2-methoxyethyl acrylate, 30 parts by weight of N-vinyl-2-pyrrolidone, and 5 parts by weight of acrylic acid, the dressing for wound of the present invention was obtained. The 50% modulus thereof was 23.3 g/mm$^2$ and the water absorption was 1,720%.

EXAMPLE 5

In a closed-type reaction vessel equipped with a stirrer were placed 0.05 part by weight of 1-(4-isopropylphenyl)-2-hydroxy-2-methylpropan-1-one, 80 parts by weight of 2-methoxyethyl acrylate, and 20 parts by weight of N-vinyl-2-pyrrolidone. After replacing the inside atmosphere of the reaction vessel with a nitrogen gas at a flow rate of 10 ml/minute for 2 hours, the mixture was irradiated with UV rays at a dose of about 50 mj/cm$^2$ to obtain a partially photopolymerized syrup.

The syrup was flow-cast in a silicone-made frame having a thickness of 1.2 mm disposed on a releasable PET film subjected to a silicone treatment and after covering thereon with a similar releasable PET film, the flow-cast layer was uniformly irradiated from both sides with UV rays at total doses of 3,000 mg/cm$^2$. The film thus formed was dried at 130° C. for 30 minutes to obtain the dressing for wound of the present invention as a transparent sheet having a thickness of 1 mm. The 50% modulus thereof was 17.7 g/mm$^2$ and the water absorption thereof was 370%.

EXAMPLE 6

By following the same procedure as in Example 5 except that the monomer composition was 70 parts by weight of 2-methoxyethyl acrylate and 30 parts by weight of N-vinyl-2-pyrrolidone, the dressing for wound of the present invention was obtained. The 50% modulus thereof was 24.7 g/mm$^2$ and the water absorption was 1,900%.

EXAMPLE 7

By following the same procedure as in Example 5 except that the monomer composition was 65 parts by weight of 2-methoxyethyl acrylate, 30 parts by weight of N-vinyl-2-pyrrolidone, and 5 parts by weight of acrylic acid, the dressing for wound of the present invention was obtained. The 50% modulus thereof was 39.2 g/mm$^2$ and the water absorption was 4,850%.

EXAMPLE 8

In a closed-type reaction vessel equipped with a stirrer were placed 0.05 part by weight of 1-(4-isopropylphenyl)-2-hydroxy-2-methylpropan-1-one, 49 parts by weight of 2-methoxyethyl acrylate, and 21 parts by weight of N-vinyl-2-pyrrolidone. After replacing the inside atmosphere of the reaction vessel with a nitrogen gas at a flow rate of 10 ml/minute for 2 hours, the mixture was irradiated with UV rays at total doses of about 50 mj/cm$^2$ to obtain a partially photopolymerized syrup.

To the syrup was added 30 parts by weight of polyoxypropylene glycol having an average molecular weight of 400 and the resulting mixture was stirred for one hour in a nitrogen gas stream. The reaction mixture obtained was flow-cast in a silicone-made frame having a thickness of 1.2 mm disposed on a releasable PET film subjected to a silicone treatment and after covering thereon with a similar releasable PRT film, the flow-cast layer was uniformly irradiated from both sides with UV rays at a total dose of 3,000 mj/cm$^2$ while properly air-cooling under an inert atmosphere. After drying at 130° C. for 30 minutes, the dried film was irradiated with γ-rays at a dose of 50 kGy to obtain the dressing for wound of the present invention as a transparent sheet having a thickness of 1 mm. The 50% modulus thereof was 2.1 g/mm$^2$ and the water absorption was 1,080%.

EXAMPLE 9

By enclosing the dressing for wound of the present invention obtained in Example 4 in a gas permeable bacteria-resisting package and sterilizing it with an ethylene oxide gas, the medical bandage of the present invention was obtained.

EXAMPLE 10

By enclosing the sample obtained in Example 7 before the irradiation with γ-rays in a package, and then irradiating the package containing the sample with γ-rays at a dose of 25 kGy, the medical bandage of the present invention was obtained.

EXAMPLE 11

The copolymer solution obtained in Example 1 was coated on a releasable PET film having a thickness of 50 μm at a definite thickness. After drying at 130° C. for 5 minutes, the coated layer was transferred onto a polyurethane film having a thickness of 75 μm to obtain the medical bandage having a 30 μm thick water-absorptive polymer layer of the present invention.

EXAMPLE 12

The syrup containing the plasticizer obtained in Example 8 was coated on a releasable PET film having a thickness of 50 μm at a definite thickness. After covering thereon with a similar releasable PET film, the assembly was irradiated with UV rays at a total dose of 3,000 mj/cm$^2$ while cooling under an inert gas atmosphere. One of the releasable films was removed. After drying the coated layer at 130° C. for 5 minutes, the coated layer was transferred onto a polyurethane film having a thickness of 75 μm, and the transferred layer was irradiated with γ-rays at a dose of 50 kGy to obtain the medial bandage having a 30 μm thick water-absorptive polymer layer of the present invention.

EXAMPLE 13

In a closed-type reaction vessel equipped with a stirrer were placed 0.05 part by weight of 1-(4-isopropylphenyl)-2-hydroxy-2-methylpropan-1-one, 56 parts by weight of 2-methoxyethyl acrylate, and 24 parts by weight of N-vinyl-2-pyrrolidone. After replacing the inside atmosphere of the reaction vessel with a nitrogen gas at a flow rate of 10 ml/minute for 2 hours, the mixture was irradiated with UV rays at total doses of about 50 mj/cm$^2$ to obtain a partially photopolymerized syrup.

To 70 parts by weight of the syrup were added 0.18 part by weight of polyethylene glycol 600 dimethacrylate and 30 parts by weight of polyoxypropylene glycol having an average molecular weight of 400 and the mixture was stirred for one hour under a nitrogen gas stream. The reaction mixture obtained was flow-cast in a silicone-made frame having a thickness of 1.2 mm disposed on a releasable PET film subjected to a silicone treatment and after covering thereon with a similar releasable PET film, the assembly was uniformly irradiated from both sides with UV rays at total doses of 3,000 mj/cm$^2$ while properly air-cooling under an inert atmosphere. By drying at 130° C. for 30 minutes, the dressing for wound of the present invention was obtained as a transparent sheet having a thickness of 1 mm. The 50% modulus thereof was 2.1 g/mm$^2$ and the water absorption was 740%.

EXAMPLE 14

In a closed-type reaction vessel equipped with a stirrer were placed 0.05 part by weight of 1-(4-isopropylphenyl)-2-hydroxy-2-methylpropan-1-one, 49 parts by weight of 2-methoxyethyl acrylate, and 21 parts by weight of N-vinyl-2-pyrrolidone. After replacing the inside atmosphere of the reaction vessel with a nitrogen gas at a flow rate of 10 ml/minute for 2 hours, the mixture was irradiated with UV rays at total doses of about 50 mj/cm$^2$ to obtain a partially photopolymerized syrup.

To 70 parts by weight of the syrup were added 0.18 part by weight of polyethylene glycol 600 dimethacrylate and 30 parts by weight of polyoxypropylene glycol having an average molecular weight of 400 and the mixture was stirred for one hour under a nitrogen gas stream. The reaction mixture obtained was flow-cast in a silicone-made frame having a thickness of 1.2 mm disposed on a releasable PET film subjected to a silicone treatment and after covering thereon with a similar releasable PET film, the assembly was uniformly irradiated from both sides with UV rays at total doses of 3,000 mj/cm$^2$ while properly air-cooling under an inert atmosphere. By further drying at 130° C. for 30 minutes, the dressing for wound of the present invention was obtained as a transparent sheet having a thickness of 1 mm. The 50% modulus thereof was 2.1 g/mm$^2$ and the water absorption was 740%.

EXAMPLE 15

By following the same procedure as in Example 13 except that the monomer composition excluding the multifunctional acrylate or methacrylate was 65 parts by weight of 2-methoxyethyl acrylate, 30 parts by weight of N-vinyl-2-pyrrolidone, and 5 parts by weight of acrylic acid, the dressing for wound of the present invention was obtained. The 50% modulus thereof was 3.5 g/mm$^2$ and the water absorption was 1,700%.

EXAMPLE 16

By enclosing the dressing for wound of the present invention obtained in Example 13 in a gas permeable bacteria resisting package and sterilizing the material with an ethylene oxide gas, the medical bandage of the present invention was obtained.

EXAMPLE 17

By enclosing the dressing for wound obtained in Example 13 in a package, and then irradiating the assembly with γ-rays at a dose of 25 kGy, the medical bandage of the present invention was obtained. The 50% modulus thereof was 2.5 g/mm$^2$ and the water absorption thereof was 630%.

EXAMPLE 18

The syrup containing the multifunctional acrylate or methacrylate and the plasticizer obtained in Example 13 was coated on a releasable PET film having a thickness of 50 μm at a definite thickness and after covering thereon with a similar releasable PET film, the coated layer was irradiated with UV rays at total doses of 3,000 mj/cm$^2$ while cooling under an inert atmosphere. One of the releasable films was removed and after drying at 130° C. for 5 minutes, the coated layer thus dried was transferred onto a polyurethane film having a thickness of 75 μm to obtain the medical bandage having a 30 μm thick water-absorptive polymer layer of the present invention.

COMPARATIVE EXAMPLE 1

By following the same procedure as in Example 1 except that the monomer composition was 90 parts by weight of 2-methoxyethyl acrylate and 10 parts by weight of N-vinyl-2-pyrrolidone, a polymer was obtained. The polymer thus obtained was a liquid product having a high viscosity at normal temperature, and the 50% modulus thereof could not be measured due to the poor shape-retention property. Further, the water absorption thereof was 15%.

COMPARATIVE EXAMPLE 2

By following the same procedure as in Example 1 except that the monomer composition was 50 parts by weight of 2-methoxyethyl acrylate and 50 parts by weight of N-vinyl-2-pyrrolidone, a polymer was obtained. The 50% modulus thereof was 70.5 g/mm$^2$ and the polymer was dissolved without being swelled in a water absorption test.

COMPARATIVE EXAMPLE 3

By following the same procedure as in Example 8 except that the composition of the photopolymerization initiator, the monomers, and the plasticizer was 0.025 part by weight of 1-(4-isopropylphenyl)-2-hydroxy-2-methylpropan-1-one, 35 parts by weight of 2-methoxyethyl acrylate, 15 parts by weight of N-vinyl-2-pyrrolidone, and 50 parts by weight of polyoxypropylene glycol having an average molecular weight of 400, respectively, a polymer composition was obtained. The polymer composition was a viscous liquid having a small cohesive force, the 50% modulus thereof could not be measured, and the polymer was dissolved without being swelled in a water absorption test.

COMPARATIVE EXAMPLE 4

A polyether polyamide block polymer film having a thickness of 30 μm was used as a support layer and by laminating thereon an acrylic pressure-sensitive adhesive layer (having a thickness of 50 μm) comprising isononyl acrylate/2-methoxyethyl acrylate/acrylic acid (65/30/5 by weight ratio), a film dressing was obtained.

COMPARATIVE EXAMPLE 5

A polyurethane film having a thickness of 30 μm was used as a support layer and by laminating thereon a pressure-sensitive adhesive sheet (having a thickness of 1 mm) comprising a kneaded mixture of 47 parts by weight of polyisobutyrene and 53 parts by weight of hydrocolloid, a hydrocolloid dressing was obtained.

In addition, the hydrocolloid used had a composition comprising 17.5 parts by weight of carboxymethyl cellulose Na, 12.5 parts by weight of pectin, 19.5 parts by weight of gelatin, 3.0 parts by weight of potassium alum, and 0.5 part by weight of white vaseline.

COMPARATIVE EXAMPLE 6

By irradiating a 4 wt % aqueous solution of polyoxyethylene with γ-rays as in Example 1, a hydrogel dressing having a thickness of 1 mm was obtained.

COMPARATIVE EXAMPLE 7

By following the same procedure as in Example 1 except that the monomer composition was 0.005 part by weight of polyethylene glycol 600 dimethacrylate, a polymer mixture was obtained. The 50% modulus thereof was 1.9 g/mm$^2$ and the polymer mixture was dissolved without being swelled in a water absorption test.

COMPARATIVE EXAMPLE 8

By following the same procedure as in Example 1 except that the monomer composition was 5 parts by weight of polyethylene glycol 600 dimethacrylate, a polymer mixture was obtained. The 50% modulus thereof was 15.0 g/mm$^2$ and the polymer mixture was whitened after swelling in a water absorption test and the transparency was greatly lowered. In addition, the water absorption was 240%.

The 50% modulus and the water absorption employed in the examples and the comparative examples were obtained by the following methods.

Tensile Test:

Each of the samples obtained in the above examples and comparative examples was cut into 2 cm×4 cm, each sample was holded at the positions 1 cm apart from both ends of the long side, a tensile test was conducted using Tensilon (STM-T-50BP), trade name, manufactured by Toyo Boldwin Co., and the stress (g/mm$^2$) at 50% tension was defined as the 50% modulus.

In this case, the distance between the chucks was 20 mm and the tensile speed was 300 mm/minute.

Water Absorption Test:

Each of the samples obtained in the above examples and comparative examples was cut into 1.5 cm × 1.5 cm and after measuring the weight of the sample before absorbing water, each sample piece was immersed in 135 ml of a phosphoric acid buffer isotonic sodium chloride solution (pH 7.4 and 32° C.) for 24 hours. Each sample piece was took out, the water on the surface thereof was wiped off, the weight after absorbing water was measured, and the water absorption was calculated from the increased weight.

On the samples of Example 1, Example 13 and Comparative Examples 4 to 6, the water absorptive property, the skin adhesive property, the flexibility, and the transparency were measured and the results are shown in Table 1 below.

TABLE 1

| | Comparative Example 4 | Comparative Example 5 | Comparative Example 6 | Example 1 | Example 13 |
|---|---|---|---|---|---|
| Water Absorptive Property | x | ∘ | Δ | ∘ | ∘ |
| Skin Adhesive Property | ∘ | ∘ | x | ∘ | ∘ |
| Flexibility | Δ | Δ | ∘ | ∘ | ∘ |
| Transparency | ∘ | x | ∘ | ∘ | ∘ |

∘: Good
Δ: Slighty Good
x: Poor

From the results shown in Table 1 above, it can be seen that the samples of Example 1 and Example 13 are all satisfactory in the water absorptive property, the skin adhesive property, the flexibility, and the transparency, but the sample of Comparative Example 4 is poor in the water absorptive property and cannot be said to sufficiently satisfy the flexibility, the sample of Comparative Example 5 is poor in the transparency and cannot be said to sufficiently satisfy the flexibility, and the sample of Comparative Example 6 is poor in the skin adhesive property and cannot be said to sufficiently satisfy the water absorptive property.

EXAMPLE 19

In a 20 liter closed-type reaction vessel equipped with a stirrer were placed 0.15 part by weight of azobisisobutyronitrile, 70 parts by weight of 2-methoxyethyl acrylate, 30 parts by weight of N-vinyl-2-pyrrolidone, and 250 parts by weight of a mixed solvent of distilled water/methanol/isopropanol (32/47/1 by weight ratio). After replacing the inside atmosphere of the reaction vessel with a nitrogen gas at a flow rate of 500 ml/minute for 2 hours, the reaction was conducted for 4 hours with stirring and while keeping the temperature in the reaction vessel at from 60°0 to 70° C. by adding dropwise the mixed solvent (30 parts by weight) to the mixture. After completion of the reaction by further stirring the mixture at 75° C. for 2 hours, the reaction mixture thus obtained was cooled to room temperature to obtain a solution of an acrylic copolymer.

By drying the solution of the acrylic copolymer with a coating machine, a medical water-absorptive polymer layer was obtained. The drying condition was as follows. The coated layer was dried for 4 minutes at a coating speed of 1.5 meters/minute, a drying tower length of 6.0 meters, and a drying temperature of from 120°0 to 140° C. in a fresh air stream. Thus, a transparent film having a thickness of 50 μm was obtained. The transparent films thus obtained were laminated each other to form a roll-formed film having an average thickness of 2 cm and cut into a long strip form having a proper size.

The long strip-form sample thus obtained was T-die molded by a single screw extruder. That is, by molding at a screw rotation number of 60 rpm, a molding temperature of from 150° to 170° C., a die lip width of 0.5 mm, a die lip length of 100 mm, and a drawing out speed of 15 m/minute, a colorless and transparent medical water-absorptive polymer layer having a thickness of 400 μm was obtained.

By covering both surfaces of the polymer layer with a releasable paper, and then irradiating the polymer layer with γ-rays at a dose of 27.7 kGy, the dressing for wound of the present invention was obtained.

The dressing for wound has excellent water absorptive property, flexibility, transparency and moisture permeability in the healing experiment for the skin cut-off wound of the back portion of a rat.

EXAMPLE 20

By adhering a polyether polyamide block copolymer film having a thickness of 30 μm to one surface of the medical water-absorptive polymer layer formed in Example 19 through the acrylic pressure-sensitive adhesive layer having a thickness of 20 μm described in Example 22, and then irradiating the polymer layer with γ-rays at a dose of 27.7 kGy, the dressing for wound of the present invention was obtained.

The dressing for wound had excellent water absorptive property, flexibility, transparency, and moisture permeability in the healing experiment for the skin cut-off wound of the back portion of a rat.

EXAMPLE 21

In a 20 liter closed-type reaction vessel equipped with a stirrer were placed 0.2 part by weight of azobisisobutyronitrile, 65 parts by weight of isononyl acrylate, 30 parts by weight of 2-methoxyethyl acrylate, 5 parts by weight of acrylic acid, and 25 parts by weight of toluene. After replacing the inside atmosphere of the reaction vessel with a nitrogen gas at a flow rate of 10 ml/minute for 2 hours, the reaction was conducted for 8 hours with stirring while keeping the inside of the reaction vessel at a temperature of from 57° to 60° C. by adding dropwise toluene (solvent)(125 parts by weight) to the mixture. By further stirring the mixture at 80° C. for 2 hours, the reaction was completed and the reaction mixture was cooled to room temperature to obtain a solution of an acrylic copolymer.

The solution of the acrylic copolymer was coated on a releasable paper at a definite thickness followed by drying at 110° C. for 2 minutes in a fresh stream, whereby an acrylic pressure-sensitive adhesive layer having a high moisture permeability and a thickness of 20 μm was obtained.

The acrylic pressure-sensitive adhesive layer was punched by a projection-having roll to obtain a porous (hole-having) pressure-sensitive adhesive layer having circular holes having a diameter of 0.8 mm arranged lattice-like at an interval of 2.0 mm and having a porosity per unit area of 12.6%.

The porous pressure-sensitive film was adhered to the medical dressing obtained in Example 19 and after covering both surfaces of the laminate with a releasable paper, the assembly was irradiated with γ-rays at a dose of 27.7 kGy, whereby the dressing for wound of the present invention wherein the 50% modulus of the medical water-absorptive polymer layer was 23.6 g/mm$^2$ and the water absorption thereof was 710% was obtained.

The dressing for wound had excellent water absorptive property, flexibility, transparency, moisture permeability, and sealing property and in the healing experiment for the skin cut-off wound of the back portion of a rat, the infection of bacteria was scarecely found, that is, the dressing for wound showed an excellent healing result.

EXAMPLE 22

By adhering a polyether polyamide block copolymer film having a thickness of 30 μm to the laminate of the γ-ray irradiated sheet-form medical water-absorptive polymer layer and the porous pressure-sensitive adhesive layer obtained in Example 21 at the opposite side to the porous pressure-sensitive adhesive layer side as a backing material through the acrylic pressure-sensitive adhesive layer described in Example 21, and then irradiating the assembly with γ-rays at a dose of 27.7 kGy, the dressing for wound of the present invention having excellent antibacterial property was obtained.

The dressing for wound also had excellent water absorptive property, flexibility, transparency, and sealing property, and in the healing experiment for the skin cut-off wound of the back portion of a rat, the infection of bacteria was scarecely found, that is, the dressing for wound showed an excellent healing result.

EXAMPLE 23

In a 20 liter closed-type reaction vessel equipped with a stirrer were placed 0.2 part by weight of azobis-isobutyronitrile, 70 parts by weight of 2-methoxyethyl acrylate, 30 parts by weight of N-vinyl-2-pyrrolidone, and 66.7 parts by weight of toluene. After replacing the inside atmosphere of the reaction vessel with a nitrogen gas at a flow rate of 500 ml/minute for 2 hours, the reaction was conducted for 4 hours with stirring while keeping the inside of the reaction vessel at a temperature of from 58° to 68° C. by adding dropwise the solvent (166.7 parts by weight). By further stirring the mixture at 80° C. for 2 hours, the reaction was completed and the reaction mixture formed was cooled to room temperature to obtain a solution of an acrylic copolymer.

By coating the solution of the acrylic copolymer on a releasable paper at a definite thickness, and then drying the coated layer at 130° C. for 5 minutes in a fresh air stream, a colorless transparent film-form medical water-absorptive polymer layer having a thickness of 50 μm was obtained.

To one surface of the medical water-absorptive polymer layer was adhered the same porous pressure-sensitive adhesive layer as in Example 21 and to the other surface thereof was adhered a polyether polyamide block copolymer film having a thickness of 20 μm through the acrylic pressure-sensitive adhesive layer described in Example 22 as a backing material. After covering both surfaces of the laminate with a releasable paper, the assembly was irradiated with γ-rays at a dose of 26.9 kGy to obtain the medical bandage of the present invention wherein the 50% modulus of the medical water-absorptive polymer layer was 21.1 g/mm$^2$ and the water absorption thereof was 1,030%.

When the medical bandage thus obtained was adhered to a normal skin showing much perspiration and the state thereof was observed after 8 hours since adhering, the occurrence of stuffiness at the adhered portion was scarecely observed or clearly slight and the peeling of the bandage at the peripheral portion was not observed. Also, the skin stimulation such as an erthema, an itch, etc., was not observed.

EXAMPLE 24

In Example 21 and Example 22, after enclosing each of the laminates before the irradiation with γ-rays in an antibacterial package, each laminate was irradiated with γ-rays at a dose of 27.7 kGy to obtain each of the dressings for wound of the present invention.

EXAMPLE 25

In Example 23, after enclosing the laminate before the irradiation with γ-rays in an antibacterial package, the laminate was irradiated with γ-rays at a dose of 26.9 kGy to obtain the medical bandage of the present invention.

In addition, the 50% modulus and the water absorption in Examples 21 and 23 described above were obtained by the methods described above.

EXAMPLE 26

In a 20 liter closed-type reaction vessel equipped with a stirrer were placed 0.175 part by weight of azobis-isobutyronitrile, 70 parts by weight of 2-methoxyethyl acrylate, 30 parts by weight of N-vinyl-2-pyrrolidone, and 250 parts by weight of a mixed solvent of distilled water/methanol/isopropanol (16/23/1 by weight ratio). After replacing the inside atmosphere of the reaction vessel with a nirtogen gas at a flow rate of 10 ml/minute for 2 hours, the mixture was stirred for 1.5 hours while keeping the inside of the reaction vessel at a temperature of from 60° to 62° C. By further stirring the mixture at 75° C. for 2 hours, the reaction was completed and the reaction mixture was cooled to room temperature to obtain a solution of an acrylic compound.

By coating the solution of the acrylic copolymer on a releasable paper at a definite thickness, and then drying at 130° C. for 5 minutes, the solvents and the unreacted monomers were removed and the medical water-absorptive polymer was obtained as a transparent film having a thickness of 50 μm. The amounts of 2-methoxyethyl acrylate and N-vinyl-2 -pyrrolidone in the medical water-absorptive polymer were less than 10 ppm by weight and 200 ppm by weight, respectively.

EXAMPLE 27

In a 20 liter closed-type reaction vessel were placed 0.175 part by weight of azobis-isobytonitrile, 70 parts by weight of 2-methoxyethyl acrylate, 30 parts by weight of N-vinyl-2-pyrrolidone, and 150 parts by weight of toluene. After replacing the inside atmosphere of the reaction vessel with a nitrogen gas, the mixture was stirred for 9 hours while keeping the inside of the reaction vessel at a temperature of from 60° to 62° C. 83.3 Parts by weight of toluene was added to the reaction mixture and after stirring the resulting mixture at 80° C. for 2 hours to complete the reaction, the reaction mixture was cooled to room temperature to obtain a solution of an acrylic copolymer.

By coating the solution of the acrylic copolymer on a releasable paper at a definite thickness, and then drying at 130° C. for 5 minutes, the solvent and the unreacted monomers were removed and the medical water-absorptive polymer layer was obtained as a transparent film having a thickness of 50 μm. The amounts of 2-methoxyethyl acrylate and N-vinyl-2-pyrrolidone in the medical water-absorptive polymer were less than 10 ppm by weight and 180 ppm by weight, respectively.

EXAMPLE 28

In a 20 liter closed-type reaction vessel were placed 0.175 part by weight of azobis-isobutyronitrile, 65 parts by weight of 2-methoxyethyl acrylate, 30 parts of N-vinyl-2-pyrrolidone, 5 parts by weight of acrylic acid, and 150 parts by weight of toluene. After replacing the inside atmosphere of the reaction vessel with a nitrogen gas at a flow rate of 10 ml/minute for 2 hours, the mixture was stirred for 8 hours while keeping the inside of the reaction vessel at a temperature of from 60° to 62° C. 83.3 Parts by weight of toluene was added thereto and after further stirring the mixture at 80° C. for 2 hours to complete the reaction, the reaction mixture formed was cooled to room temperature to obtain a solution of an acrylic copolymer.

By coating the solution of the acrylic copolymer on a releasable paper at a definite thickness, and then drying the coated layer at 130° C. for 5 minutes, the solvent and the unreacted monomers were removed to obtain the medical water-absorptive polymer layer of the present invention as a transparent film having a thickness of 50 μm. The amounts of 2-methoxyethyl acrylate, N-vinyl-2-pyrrolidone, and acrylic acid in the medical water-absorptive polymer were less than 10 ppm by weight, 220 ppm by weight and 5 ppm by weight, respectively.

EXAMPLE 29

In a 20 liter closed-type reaction vessel equipped with a stirrer were placed 0.15 part by weight of azobisisobutyronitrile, 70 parts by weight of 2-methoxyethyl acrylate, 30 parts by weight of N-vinyl-2-pyrrolidone, and 250 parts by weight of a mixed solvent of distilled water/methanol/isopropanol (32/47/1 by weight). After replacing the inside of the reaction vessel with a nitrogen gas at a flow rate of 500 ml/minute for 2 hours, the reaction was conducted for 4 hours with stirring while keeping the inside of the reaction vessel at a temperature of from 60° to 70° C. by adding dropwise thereto the mixed solvent (30 parts by weight). After further stirring the mixture at 75° C. for 2 hours to complete the reaction, the reaction mixture was cooled to room temperature to obtain a solution of an acrylic copolymer.

The solution of the acrylic copolymer was dried by a coating machine to obtain a medical water-absorptive polymer layer. That is, the coated layer was dried at a coating speed of 1.5 m/minute, a drying tower length of 6.0 meters, a drying time of 4 minutes, and a drying temperature of from 120° C. to 140° C. in a fresh air stream to obtain a transparent film having a thickness of 50 μm. The transparent films thus obtained were laminated to form a roll-form film having a thickness of 2 cm and the roll film was cut into a long strip-form film having a proper size. The amounts of 2-methoxyethyl acrylate and N-vinyl-2-pyrrolidone in the medical water-absorptive polymer layer were less than 10 ppm by weight and 130 ppm by weight, respectively.

The long strip-form sample was T-die molded by a single screw extruder. That is, by molding at a screw rotation number of 60 rpm, a molding temperature of from 150° to 170° C., a die lip width of 0.5 mm, a die lip length of 100 mm, and a drawing out speed of 15 m/minute, a colorless transparent sheet having an average thickness of 400 μm was obtained.

Furthermore, the sheet was irradiated with γ-rays at a dose of 27.7 kGy to obtain the medical bandage of the present invention. The 50% modulus of the medical bandage was 23.6 g/mm² and the water absorption was 710%.

EXAMPLE 30

In a 20 liter closed-type reaction vessel equipped with a stirrer were placed 0.2 part by weight of azobisisobutyronirile, 70 parts by weight of 2-methoxyethyl acrylate, 30 parts by weight of N-vinyl-2-pyrrolidone, and 66.7 parts by weight of toluene. After replacing the inside atmosphere of the reaction vessel with a nitrogen gas at a flow rate of 500 ml/minute for 2 hours, the reaction was conducted with stirring while keeping the inside of the reaction vessel at a temperature of from 58° to 68° C. by adding dropwise thereto the mixed solvent (166.7 parts by weight). By further stirring the mixture at 80° C. for 2 hours to complete the reaction, the reaction mixture was cooled to room temperature to obtain a solution of an acrylic copolymer.

By coating the solution of the acrylic copolymer on a releasing paper at a definite thickness, and then drying the coated layer at 130° C. for 5 minutes to remove the solvent and the unreacted monomers, a medical water-absorptive polymer layer was obtained as a transparent film having a thickness of 50 μm. The amounts of 2-methoxyethyl acrylate and N-vinyl-2-pyrrolidone in the medical water-absorptive polymer layer were less than 10 ppm by weight and 130 ppm by weight, respectively.

By drying the solution of the acrylic copolymer by a coating machine, a medical water-absorptive polymer layer was obtained. That is, by drying the coated layer at a coating speed of 1.5 m/minute, a drying tower length of 6.0 meters, a drying time of 4 minutes, and a drying temperature of from 120° to 140° C. in a fresh air stream, a transparent film having a thickness of 50 μm was obtained. The transparent films were laminated to form a roll-form film having a thickness of 2 cm and the roll film was cut into a long strip-form film having a proper size.

The long strip-form sample was T-die molded by a single screw extruder. That is, by modling the sample at a rotation number of 40 rpm, a molding temperature of from 150° to 170° C., a die lip width of 0.5 mm, a die lip length of 100 mm, and a drawing speed of 30 m/minute, a colorless transparent sheet having an average thickness of 100 μm was obtained.

Furthermore, by irradiating the sheet with γ-rays at a rose of 26.9 kGy, the medical dressing of the present invention was obtained. The 50% modulus of the medical dressing (medical water-absorptive polymer layer) was 21.2 g/mm² and the water absorption was 1,030%.

EXAMPLE 31

In Example 29, three extruded sheets before the irradiation with γ-rays were laminated and after heat-pressing the laminate, the laminate was irradiated with γ-rays at a dose of 27.7 kGy to obtain the medical dressing of the present invention as a sheet having a thickness of 1.1 mm.

EXAMPLE 32

In Example 29, after enclosing the excluded sheet before the irradiation with γ-rays in an antibacterial package, the sheet was irradiated with γ-rays at a dose of 27.7 kGy to obtain the dressing for wound of the present invention.

EXAMPLE 33

In Example 33, after adhering a nonwoven fabric having a thickness of 50 μm to the extruded sheet before the irradiation with γ-rays by heat-pressing, the sheet was irradiated with γ-rays at a dose of 27.7 kGy, and the medical bandage of the present invention was obtained.

EXAMPLE 34

In a 20 liter closed-type reaction vessel equipped with a stirrer were placed 0.05 part by weight of 1-(4-isopropylphenyl)-2-hydroxy-2-methylpropan-1-one, 70 parts by weight of 2-methoxyethyl acrylate, and 30 parts by weight of N-vinyl-2-pyrrolidone. After replacing the inside atmosphere of the reaction vessel with a nitrogen gas at a flow rate of 10 ml/minute for 2 hours, the mixture was irradiated with UV rays at total doses of 50 Mj/cm$^2$ to obtain a partially photopolymerized syrup.

The syrup was flow-cast in a silicone-made frame having a thickness of 1.2 mm disposed on a releasable PET film subjected to a silicone treatment and after covering thereon with a similar releasing PET film, the flow-cast layer was uniformly irradiated from both sides with UV rays at a total doses of 3,000 mJ/cm$^2$ while properly air-cooling in an inert atmosphere. By drying it at 130° C. for 30 minutes, the medical bandage of the present invention was obtained as a transparent sheet having a thickness of 1 mm.

The amounts of 2-mehoxyethyl acrylate and N-vinyl-2-pyrrolidone on the polymer after drying were 190 ppm by weight and 1,020 ppm by weight, respectively. Also, the 50% modulus thereof was 20.0 g/mm$^2$ and the water absorption was 1,100%.

EXAMPLE 35

By following the same procedure as in Example 34 except that the monomer composition was 65 parts by weight of 2-methoxyethyl acrylate, 30 parts by weight of N-vinyl-2-pyrrolidone, and 5 parts by weight of acrylic acid, the medical bandage of the present invention was obtained. The amounts of 2-methoxyethyl acrylate, N-vinyl-2-pyrrolidone, and acrylic acid in the polymer after drying were 250 ppm by weight, 1,530 ppm by weight, and 360 ppm by weight, respectively.

In addition, the monomer amounts in the above examples were obtained by the following method and the 50% modulus and the water absorption shown in the above examples were obtained by the methods described above.

Residual Monomer Determination Test:
(Amounts of 2-methoxyethyl acrylate and N-vinyl-2-pyrroidone)

To 0.5 g of each of the samples obtained in the examples described above was added 10 ml of ethyl acetate and after extracting by shaking the mixture for 3 hours at 150 rpm, the extract was allowed to stand for 2 days. The extract was analyzed using an HP5890A-type gas chromatographic apparatus (manufactured by Yokogawa-Hewlett-Packard, Ltd) and from the calibration curve prepared using a standard reagent, the monomer amounts were calculated.

(Amount of Acrylic Acid)

To 0.1 g of each of the samples obtained in the examples described above was added 10 ml of acetonitrile and after extracting by shaking the mixture for 3 hours at 150 rpm, the extract was allowed to stand for 2 days. The extract was analyzed using a CCPM(UV8000)-type high-speed liquid chromatographic apparatus (manufactured by Nippon Bunko K.K.) and from the calibration curve prepared using a standard reagent, the monomer amount was calculated.

Since the medical water-absorptive polymer of the present invention has the construction as described above and the polymer is obtained by copolymerizing specific hydrophilic monomers, the medical water-absorptive polymer has the excellent flexibility and water absorbing and swelling property and also has the effect that the skin adhesive property and the transparency are excellent.

Further, the medical water-absorptive polymer of the present invention obtained by photopolymerizing the above-described specific monomers further containing the multifunctional acrylate or methacrylate has the excellent flexibility and water absorbing and swelling property and also has the effect that the skin adhesive property and the transparency are excellent.

Furthermore, in the medical water-absorptive polymer of the present invention obtained by crosslinking the mixture of the specific hydrophilic monomers and the plasticizer, by controlling the condition of crosslinking, the polymer having the desired various characteristics can be very easily obtained.

Since in the dressing for wound of the present invention, the medical water-absorptive polymer is formed into a film form or a sheet form, or the medical water-absorptive polymer is formed into a mesh form or porous form, the application thereof to an outer skin is very easy and the handling property is very improved. Thus, the dressing for wound of the present invention is very useful. In this case, by covering one surface of the film or sheet thus formed with a backing material, the strength, the fixing property, the form-retention property, the adhesive property, etc., of the dressing for wound are improved and also by enclosing the film or sheet in an antibacterial package in a sterilized state, the dressing for wound requiring a sterilized state is more useful.

The medical bandage of the present invention has an adhesive property to the wounded portion of a skin and since a proper pressure-sensitive adhesive property is imparted by controlling the monomer composition and the amount of the plasticizer of the acrylic copolymer, if desired, by incorporating a drug in the water-absorptive polymer layer, the medical bandage of the present invention can be also used as a transdermal drug delivery patch.

When the dressing for wound and the medical bandage of the present invention have the porous pressure-sensitive adhesive layer, the skin adhesive property is greatly improved while maintaining the excellent water absorptive property, the flexibility, and the transparency, whereby the infection with bacteria due to the poor sealing property and decrease in the adhesive force, and the occurrence of the skin stimulation caused by maceration can be prevented.

That is, when the porous pressure-sensitive layer is formed on the surface of the dressing for wound of the present invention at the side of a wounded portion, the pressure-adhesive property to the applied portion is improved to improve the sealing property, and a body fluid is efficiently absorbed through the holes or pores and also since a part of water thus absorbed and retained gradually evaporates off, the accumulation of an exudate is restrained and a wet environment suitable of healing a wound is maintained. Also, the porous pressure-sensitive layer contacted with a normal skin surrounding a wound shows an excellent adhesive property, whereby a sufficient sealing property for the prevention of the infection of bacteria is obtained.

Also, in the dressing for wound of the present invention having the construction as described above, sweet at the adhered portion thereof reaches the water absorptive polymer layer through the voids of the porous pressure-sensitive adhesive layer and is quickly absorbed therein, whereby the occurrence of maceration and the inflammation caused thereby and decrease in the adhesive force can be prevented.

Accordingly, since the dressing for wound of the present invention has excellent sealing property, elasticity, and transparency and can maintain a suitable wet environment for wet healing of a skin wound, the dressing for wound of the present invention can be used to heal a skin wound such as a dermal burn, a partial thickness wound, an incised wound, a contused wound, a sore, a suturus wound, a dermal ulcer, etc.

Furthermore, the medical bandage of the present invention has excellent skin adhesive property, water absorptive property, and moisture permeability capable of preventing the occurrence of maceration frequently causing at a much sweet portion and the inflammation caused thereby and can be more suitably used as medical pressure-sensitive sheets used as a fixing surgical tape, a first-acid bandage, a magnetic bandage, etc.; a pressure-sensitive bandage having an elasticity; a transdermal drug delivery patch preparation, etc.

In the dressing for wound and the medical bandage of the present invention, by reducing the amounts of impurities and the residual monomers, the quality thereof is stabilized and also the bad influences on a living body based on the impurities and the residual monomers can be removed, whereby safety thereof is improved.

In the dressing for wound of the present invention, by reducing the amounts of impurities and the residual monomers, the water absorptive property, the flexibity, and the transparency can be more improved and a very suitable wet environment for wet healing of a skin wound can be provided, whereby the dressing for wound of the present invention having small contents of impurities and the residual monomers can be more suitably used to heal a skin wound such as a dermal burn, a partial thickness wound, an incised wound, a contused wound, a sore, a suturus wound, a dermal ulcer, etc.

Also, in the medical bandage of the present invention, by reducing the amounts of impurities and the residual monomers, the water absorptive property and the moisture permeability capable of preventing the occurrences of maceration frequently caused at much sweet portion and the inflammation caused thereby are greatly improved and thus the medical bandage of the present invention having small contents of impurities and the residual monomers can be more suitably used as medical pressure-sensitive sheets used as a fixing surgical tape, a first-acid bandage, a magnetic plaster, etc.; a pressure-sensitive adhesive bandage having an elasticity; a transdermal drug delivery patch preparation, etc.

While the invention has been described in detail and with reference to specific embodiments thereof, it will be apparent to one skilled in the art that various changes and modifications can be made therein without departing from the spirits and scope thereof.

What is claimed is:

1. A medical water-absorptive polymer comprising an acrylic copolymer obtained by copolymerizing an acrylic composition comprising from 60 to 80% by weight of an alkoxyalkyl acrylate, from 20 to 40% by weight of an N-vinyllactam, and 10% by weight or less of a vinylcarboxylic acid.

2. The medical water-absorptive polymer of claim 1, wherein the acrylic composition is further compounded with from 0.01 to 1% by weight of a multifunctional acrylate or methacrylate.

3. The medical water-absorptive polymer of claim 1, wherein the acrylic copolymer is further compounded with 40% by weight or less of a plasticizer and said acrylic copolymer and said plasticizer are crosslinked.

4. The medical water-absorptive polymer of claim 1, wherein the acrylic copolymer is subjected to a crosslinking treatment.

5. A dressing for a wound comprising a film or a sheet formed from the medical water-absorptive polymer claimed in claim 1.

6. The dressing for a wound of claim 5, wherein the film or the sheet is crosslinked.

7. The dressing for a wound of claim 5, wherein the film or the sheet is dried.

8. The dressing for a wound of claim 5, wherein a porous or hole-having pressure-sensitive adhesive layer is formed on the surface of the dressing for wound at the adhering side to a wounded portion.

9. The dressing for a wound of claim 8, wherein a backing material is formed on the surface of the dressing for a wound opposite the side having the porous or hole-having pressure-sensitive adhesive layer.

10. A medical bandage comprising a film or a sheet formed from the medical water-absorptive polymer claimed in claim 1.

11. The medical bandage of claim 10, wherein the film or the sheet is crosslinked.

12. The medical bandage of claim 10, wherein the film or the sheet is dried.

13. The medical bandage of claim 10, wherein a porous or hole-having pressure-sensitive adhesive layer is formed on the surface of the medical bandage at the adhering side to a wounded portion.

14. The medical bandage of claim 13, wherein a backing material is formed at the side of the medical bandage opposite the side having the porous or hole-having pressure-sensitive adhesive layer.

* * * * *